(12) United States Patent
Tavernier et al.

(10) Patent No.: US 12,065,415 B2
(45) Date of Patent: Aug. 20, 2024

(54) PROCESS FOR THE PRODUCTION OF A POLYBENZOXAZINE MONOMER

(71) Applicants: ARIANEGROUP SAS, Paris (FR); CENTRE NATIONAL DE LA RECHERCHE SCIENTIFIQUE, Paris (FR)

(72) Inventors: Romain Tavernier, Doullens (FR); Lérys Granado, Carcassonne (FR); Ghislain David, Montpellier (FR); Sylvain Caillol, Montpellier (FR); Gabriel Foyer, Merignac (FR)

(73) Assignees: ARIANEGROUP SAS, Les Mureaux (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 556 days.

(21) Appl. No.: 17/437,315

(22) PCT Filed: Mar. 10, 2020

(86) PCT No.: PCT/FR2020/050484
§ 371 (c)(1),
(2) Date: Sep. 8, 2021

(87) PCT Pub. No.: WO2020/188182
PCT Pub. Date: Sep. 24, 2020

(65) Prior Publication Data
US 2022/0177437 A1    Jun. 9, 2022

(30) Foreign Application Priority Data
Mar. 15, 2019 (FR) ........................ 1902694

(51) Int. Cl.
*C07D 265/16* (2006.01)
*B64G 99/00* (2009.01)
(Continued)

(52) U.S. Cl.
CPC .......... *C07D 265/16* (2013.01); *B64G 99/00* (2022.08); *C07D 413/06* (2013.01); *C07D 413/14* (2013.01); *C08G 73/0233* (2013.01)

(58) Field of Classification Search
USPC ...................................... 528/149
See application file for complete search history.

(56) References Cited

U.S. PATENT DOCUMENTS
2017/0158877 A1    6/2017   Mcknight et al.

FOREIGN PATENT DOCUMENTS

| EP | 0659832 A1 * | 6/1995 | .............. C08L 61/06 |
| WO | WO 92/16470 A1 | 10/1992 | |
| WO | WO 01/34581 A1 | 5/2001 | |

OTHER PUBLICATIONS

Burke, et al., "Monomeric Products from the Condensation of Phenol with Formaldehyde and Primary Amines," JACS, vol. 74, No. 6, 1952, 1518-1520. (Year: 1952).*

(Continued)

*Primary Examiner* — Fred M Teskin
(74) *Attorney, Agent, or Firm* — Pillsbury Winthrop Shaw Pittman LLP

(57) ABSTRACT

A process for manufacturing a polybenzoxazine monomer, crosslinking the latter, and using the crosslinked product to form an ablative thermal protection system for a thruster nozzle or atmospheric reentry body.

9 Claims, 4 Drawing Sheets

(51) Int. Cl.
  *C07D 413/06*  (2006.01)
  *C07D 413/14*  (2006.01)
  *C08G 73/02*  (2006.01)

(56) References Cited

OTHER PUBLICATIONS

International Search Report as issued in International Patent Application No. PCT/FR2020/050484, dated Jul. 24, 2020.
Kanatomi, H., et al., "Reaction of Salicylamine with α-Dicarbonyl Compounds. II. Formation of 2,2'-Bibenz-I,3-oxazines," Bulletin of the Chemical Society of Japan, vol. 43, No. 1, Jan. 1970, pp. 226-231.
Ohashi, S., et al., "Synthesis and ring-opening polymerization of 2-substituted 1,3-benzoxazine: the first observation of the polymerization of oxazine ring-substituted benzoxazines," Polymer Chemistry, vol. 7, No. 46, Nov. 2016, pp. 7177-7184.
Tang, Z., et al., "Efficient Synthesis of 2,3-Disubstituted-1,3-benzoxazines by Chlorotrimethylsilane-Mediated Aza-Acetalizations of Aromatic Aldehydes: TMSCI-Catalyzed Synthesis of 2,3-Disubstituted-1,3-benzoxazines," Journal of Heterocyclic Chemistry, vol. 50, Aug. 2013, pp. 1116-1120.
Tang, Z., et al., "Synthesis and fungicidal activity of novel 2-aryl-3-(1,3,4-thiadiazolyl)-6(8)-methyl-1,3-benzoxazines," Bioorganic & Medicinal Chemistry Letters, vol. 25, No. 16, May 2015, pp. 3378-3381.

\* cited by examiner

PROCESS FOR THE PRODUCTION OF A POLYBENZOXAZINE MONOMER

CROSS-REFERENCE TO RELATED APPLICATIONS

This application is the U.S. National Stage of PCT/FR2020/050484, filed Mar. 10, 2020, which in turn claims priority to French patent application number 1902694 filed Mar. 15, 2019. The content of these applications are incorporated herein by reference in their entireties.

TECHNICAL FIELD

The invention relates to a process for manufacturing a polybenzoxazine monomer and crosslinking this monomer in order to form a crosslinked product having improved charring and thermal stability properties. This crosslinked product can in particular be used as an ablative resin for the construction of a thruster nozzle or an atmospheric reentry body.

PRIOR ART

Ablative thermal protection systems, such as those of thruster nozzles or atmospheric reentry bodies, are known to be made from phenolic resins synthesized from formaldehyde and phenol, in order to obtain high aromatic and crosslinking densities, and thus a high coke content. Formaldehyde and phenol are however compounds classified as carcinogenic, mutagenic and reprotoxic (CMR) category 1B and 2, whose use should be limited, in particular to anticipate possible bans in the European Union. Furthermore, the reaction of phenol and formaldehyde is a polycondensation during which water is produced. This water can be trapped in the finished product, leading to a decrease in performance. In order to solve this problem, developments have been pursued to obtain ablative resins by crosslinking benzoxazines. These developments reduce water entrapment in the finished product, but the solutions in the literature, providing a finished product with thermal stability and charring properties compatible with an application as an ablative resin, involve benzoxazines obtained by reaction of phenol with formaldehyde and an amine, and are therefore based on the use of compounds classified as CMR. Moreover, when these benzoxazines are synthesized without phenol, they exhibit poor thermal stability and charring properties.

It would therefore be desirable to have a new benzoxazine synthesis pathway that omits the use of CMR compounds and avoids the use of formaldehyde in particular.

It would also be desirable to have a new synthesis pathway for materials exhibiting thermal stability and charring properties adapted to the production of ablative thermal protection systems for thruster nozzles and atmospheric reentry bodies.

DISCLOSURE OF THE INVENTION

The invention relates to a process for manufacturing a polybenzoxazine monomer comprising condensing an amine of formula A with a polyaldehyde of formula B to obtain the polybenzoxazine monomer of formula C, formulas A, B and C being provided below:

[Chem. 1]

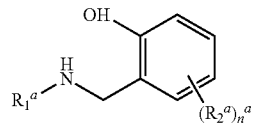

[Chem. 2]

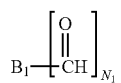

[Chem. 3]

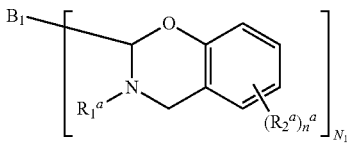

in these formulas:

$R_1^a$ is selected from: substituted or unsubstituted furfuryl groups; saturated, unsaturated or aromatic, monocyclic or polycyclic, substituted or unsubstituted carbocyclic or heterocyclic groups; substituted or unsubstituted aralkyl groups; linear or branched, saturated or unsaturated, substituted or unsubstituted hydrocarbon chains, optionally interrupted by one or more heteroatoms;

$R_2^a$ is selected from: electron-withdrawing groups; saturated or unsaturated, substituted or unsubstituted, linear or branched hydrocarbon chains comprising between 1 and 6 carbon atoms, optionally interrupted by one or more heteroatoms; saturated, unsaturated or aromatic, substituted or unsubstituted carbocyclic or heterocyclic groups;

$n^a$ is an integer comprised between 0 and 2;

$B_1$ is selected from: saturated, unsaturated or aromatic, monocyclic or polycyclic, substituted or unsubstituted carbocyclic or heterocyclic groups; linear or branched, saturated or unsaturated, substituted or unsubstituted hydrocarbon chains, optionally interrupted by one or more heteroatoms; or $B_1$ denotes a covalent bond between two aldehyde functions of formula B; and $N_1$ is an integer greater than or equal to 2.

The invention provides a new polybenzoxazine synthesis pathway that limits the use of CMR compounds and avoids the use of formaldehyde in particular. Furthermore, the product obtained by crosslinking the polybenzoxazine monomer of formula C above has high thermal stability and charring properties, compatible with an application as an ablative resin for thruster nozzles or atmospheric reentry bodies.

In an example embodiment, $R_1^a$ is selected from: substituted or unsubstituted furfuryl groups; monocyclic or polycyclic aromatic carbocyclic or aromatic heterocyclic groups; substituted or unsubstituted aralkyl groups.

The choice of such $R_1^a$ groups advantageously makes it possible to obtain, after crosslinking the polybenzoxazine monomer of formula C, a product with improved thermal stability and charring properties.

In particular, $R_1^a$ can be a substituted or unsubstituted furfuryl group.

The presence of the oxygen of the furfuryl ring provides, by accepting hydrogen bonds, further stabilization of the crosslinked network and thus an increased rate of charring.

Alternatively, $R_1^a$ is a linear or branched hydrocarbon chain. The number of carbon atoms in this hydrocarbon chain can vary in large proportions. $R_1^a$ can, for example, be a linear or branched hydrocarbon chain comprising between 1 and 20 carbon atoms or be a polymer.

In an example embodiment, $n^a$ is equal to 0.

In the alternative where $n^3$ is non-zero, $R_2^a$ can in particular be selected from: alkoxy groups; carboxyl groups; halogen atoms; saturated or unsaturated, substituted or unsubstituted, linear or branched hydrocarbon chains comprising between 1 and 6 carbon atoms, optionally interrupted by one or more heteroatoms; saturated, unsaturated or aromatic, substituted or unsubstituted carbocyclic or heterocyclic groups.

The amine of formula A can be a monoamine, i.e., with only one amine function.

In an example embodiment, the process may comprise, prior to condensation, obtaining the amine of formula A, this obtaining comprising:
- an addition reaction of an amine of formula A1 with an aldehyde of formula A2 to form an imine of formula A3, and
- a reduction reaction of the imine of formula A3 to the amine of formula A, formulas A1, A2 and A3 being provided below:

[Chem. 4]

A1

[Chem. 5]

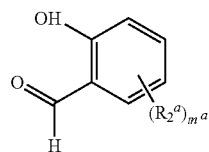

A2

[Chem. 6]

A3

The amine of formula A1 is, for example, selected from the following compounds: furfurylamine, benzylamine or 1-aminobutan-2-ol.

The aldehyde of formula A2 can, for example, be salicylaldehyde.

In an example embodiment, $B_1$ is selected from substituted or unsubstituted monocyclic or polycyclic aromatic carbocyclic or aromatic heterocyclic groups.

The choice of such a polyaldehyde advantageously makes it possible to obtain, after crosslinking the polybenzoxazine monomer of formula C, a product exhibiting improved thermal stability and charring properties.

In particular, $B_1$ can be a substituted or unsubstituted benzene ring and, in this case, $N_1=2$ or 3.

Alternatively, $B_1$ can be a linear or branched hydrocarbon chain. The number of carbon atoms in this hydrocarbon chain can vary in large proportions, $B_1$ can comprise between 1 and 20 carbon atoms or be a polymer.

The polyaldehyde of formula B is, for example, selected from the following compounds: glyoxal, glutaraldehyde, succinaldehyde, terephthalaldehyde, isophthalaldehyde.

In general, and whatever the example embodiment considered, $N_1$ can be an integer equal to 2. In this case, the polyaldehyde of formula B is a dialdehyde. Alternatively, $N_1$ can take other values, in particular $N_1$ can be equal to 3 or more.

Regardless of the embodiment considered, the condensation can be carried out by bringing the mixture of the amine of formula A with the polyaldehyde of formula B to reflux. The condensation can be carried out in toluene, methanol, ethanol or without solvent.

The invention also relates to a process for manufacturing a crosslinked product comprising crosslinking the polybenzoxazine monomer of formula C obtained by carrying out the process as described above.

This crosslinked product has a high coke content and high thermal stability, which makes it compatible with an application as an ablative resin for manufacturing a thruster nozzle or an atmospheric reentry body.

The crosslinking can be carried out by imposing a temperature greater than or equal to 130° C., for example comprised between 180° C. and 250° C.

In an example embodiment, there is crosslinking of a mixture comprising the polybenzoxazine monomer of formula C and an additional monobenzoxazine monomer of formula D, formula D being provided below:

[Chem. 7]

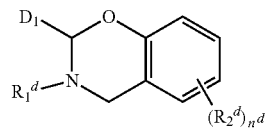

D formula in which:
$R_1^d$ is selected from: substituted or unsubstituted furfuryl groups; saturated, unsaturated or aromatic, monocyclic or polycyclic, substituted or unsubstituted carbocyclic or heterocyclic groups; substituted or unsubstituted aralkyl groups; saturated or unsaturated, substituted or unsubstituted, linear or branched hydrocarbon chains, optionally interrupted by one or more heteroatoms or by one or more saturated, unsaturated or aromatic, monocyclic or polycyclic, substituted or unsubstituted carbocyclic or heterocyclic groups;

$R_2^d$ is selected from: electron-withdrawing groups; saturated or unsaturated, substituted or unsubstituted, linear or branched hydrocarbon chains comprising between 1 and 6 carbon atoms, optionally interrupted by one or more heteroatoms; substituted or unsubstituted, saturated, unsaturated or aromatic carbocyclic or heterocyclic groups;

$n^d$ is an integer comprised between 0 and 2;

$D_1$ is selected from: saturated, unsaturated or aromatic, monocyclic or polycyclic, substituted or unsubstituted carbocyclic or heterocyclic groups; linear or branched, saturated or unsaturated, substituted or unsubstituted hydrocarbon chains, optionally interrupted by one or more heteroatoms.

The fact of adding the additional monobenzoxazine monomer of formula D facilitates the production of a liquid medium comprising the polybenzoxazine monomer of formula C at moderate temperature and without resorting to an aromatic or halogenated solvent. This facilitates the use of the mixture in processes such as resin transfer molding (RTM) without significantly affecting the thermal and charring properties of the resulting crosslinked product.

For example, it is possible to crosslink a mixture comprising the polybenzoxazine monomer of formula C in an amount of 20% to 80% by mass and preferably 20% to 50% by mass, and the additional monobenzoxazine monomer of formula D in an amount of 20% to 80% by mass and preferably 50% to 80% by mass.

In an example embodiment, $D_1$ is selected from substituted or unsubstituted monocyclic or polycyclic aromatic carbocyclic or aromatic heterocyclic groups.

In particular, $D_1$ can be a substituted or unsubstituted benzene ring.

Alternatively, $D_1$ can be a linear or branched hydrocarbon chain. The number of carbon atoms in this hydrocarbon chain can vary in large proportions, $D_1$ can comprise between 1 and 20 carbon atoms or be a polymer.

$R_1^d$ can in particular be selected from: substituted or unsubstituted furfuryl groups; monocyclic or polycyclic aromatic carbocyclic or aromatic heterocyclic groups; substituted or unsubstituted aralkyl groups. In particular, $R_1^d$ can be a substituted or unsubstituted furfuryl group. Alternatively, $R_1^d$ is a linear or branched hydrocarbon chain. The number of carbon atoms in this hydrocarbon chain can vary in large proportions. $R_1^d$ can, for example, be a linear or branched hydrocarbon chain comprising between 1 and 20 carbon atoms or be a polymer.

In an example embodiment, $n^d$ is equal to 0. In the alternative where $n^d$ is non-zero, $R_2^d$ can in particular be selected from: alkoxy groups; carboxyl groups; halogen atoms; saturated or unsaturated, substituted or unsubstituted, linear or branched hydrocarbon chains comprising between 1 and 6 carbon atoms, optionally interrupted by one or more heteroatoms; saturated, unsaturated or aromatic, substituted or unsubstituted carbocyclic or heterocyclic groups.

The additional monobenzoxazine monomer of formula D can be obtained by condensation between an amine similar to the amine of formula A with a monoaldehyde of formula $D_1$-CHO (having only one aldehyde function).

Alternatively, there is crosslinking of a mixture comprising the polybenzoxazine monomer of formula C and an additional polybenzoxazine monomer of formula E, formula E being provided below:

[Chem. 8]

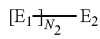

E in this formula E:

$N_2$ is an integer greater than or equal to 2;

$E_2$ is selected from saturated or unsaturated, substituted or unsubstituted, linear or branched hydrocarbon chains interrupted by one or more heteroatoms or by one or more saturated, unsaturated or aromatic, monocyclic or polycyclic, substituted or unsubstituted carbocyclic or heterocyclic groups, or uninterrupted;

the groups of formula $E_1$ are identical or different and each has the formula below:

[Chem. 9]

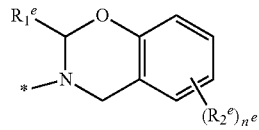

$E_1$ in this formula $E_1$:

$R_1^e$ is selected from: saturated, unsaturated or aromatic, monocyclic or polycyclic, substituted or unsubstituted carbocyclic or heterocyclic groups; linear or branched, saturated or unsaturated, substituted or unsubstituted hydrocarbon chains, optionally interrupted by one or more heteroatoms;

$R_2^e$ is selected from: electron-withdrawing groups; saturated or unsaturated, substituted or unsubstituted, linear or branched hydrocarbon chains comprising between 1 and 6 carbon atoms, optionally interrupted by one or more heteroatoms; substituted or unsubstituted, saturated, unsaturated or aromatic carbocyclic or heterocyclic groups;

$n^e$ is an integer comprised between 0 and 2;

* denotes the bond to $E_2$.

The fact of adding the additional polybenzoxazine monomer of formula E facilitates the production of a liquid medium comprising the polybenzoxazine monomer of formula C at moderate temperature and without resorting to an aromatic or halogenated solvent. This facilitates the use of the mixture in processes such as resin transfer molding (RTM) without significantly affecting the thermal and charring properties of the resulting crosslinked product.

For example, it is possible to crosslink a mixture comprising the polybenzoxazine monomer of formula C in an amount of 20% to 80% by mass, preferably 20% to 50% by mass, and the additional polybenzoxazine monomer of formula E in an amount of 20% to 80% by mass, preferably 50% to 80% by mass.

$R_1^e$ can be selected from: substituted or unsubstituted monocyclic or polycyclic aromatic carbocyclic or aromatic heterocyclic groups. In particular, $R_1^e$ can be a substituted or unsubstituted benzene ring.

In an example embodiment, $n^e$ is equal to 0. In the alternative where $n^e$ is non-zero, $R_2^e$ can in particular be selected from: alkoxy groups; carboxyl groups; halogen atoms; saturated or unsaturated, substituted or unsubstituted, linear or branched hydrocarbon chains comprising between 1 and 6 carbon atoms, optionally interrupted by one or more heteroatoms; saturated, unsaturated or aromatic, substituted or unsubstituted carbocyclic or heterocyclic groups.

$E_2$ can be selected from: linear or branched, saturated or unsaturated, substituted or unsubstituted hydrocarbon chains interrupted by one or more aromatic carbocyclic or heterocyclic groups. $E_2$ may in particular be a substituted or unsubstituted xylylene group. According to an alternative, $E_2$ can be selected from linear or branched, saturated or unsaturated, substituted or unsubstituted, uninterrupted hydrocarbon chains.

$N_2$ can be equal to 2.

In a manner similar to that described above, the compound of formula E can be obtained by condensation of a polyamine with an aldehyde of formula $R_1^e$—CHO.

Regardless of the embodiment considered, the proportion of additional monobenzoxazine monomer of formula D or additional polybenzoxazine monomer of formula E can be selected so that the mixture is liquid when heated to a temperature comprised between 20° C. and 100° C.

By way of example, each of $R_1^a$, $B_1$, $R_2^a$, $R_1^d$, $R_2^d$, $D_1$, $E_2$, $R_1^e$, $R_2^e$ can be substituted with at least one of the following groups: hydroxymethyl, methyl, carboxylic add.

The invention also relates to a process for manufacturing a thruster nozzle in which the nozzle is manufactured using a crosslinked product obtained by the process described above.

The thruster nozzle can be made of a composite material. In this case, the manufacture of the nozzle can comprise a first step of forming a fibrous preform of the nozzle to be obtained impregnated by the polybenzoxazine monomer of formula C obtained as described above or by a mixture comprising this monomer as described above. This manufacture can further comprise a second step of heat treatment of the impregnated fibrous preform so as to crosslink the polybenzoxazine monomer of formula C or the mixture and obtain the thruster nozzle.

The fibrous preform can, for example, comprise fibers of carbon, silica, glass or a ceramic material, such as silicon carbide. The fibrous preform intended to form the fibrous reinforcement of the nozzle can be formed in various ways (draping of pre-impregnated fabric layers, for example). In particular, impregnated two-dimensional or three-dimensional fabric layers can be draped or wound onto a form having a surface reproducing the desired geometry of an inner or outer surface of the nozzle to be made in order to obtain the impregnated preform. Alternatively, the fibrous preform of the nozzle to be obtained may first be obtained and then this preform can be placed in an injection cavity and then the polybenzoxazine monomer of formula C or the mixture comprising this monomer described above injected into the cavity so as to impregnate the preform. In this case, a resin transfer molding technique can be used to impregnate the fibrous preform.

The invention also relates to a process for manufacturing an atmospheric reentry body in which the atmospheric reentry body is manufactured using a crosslinked product obtained by the process described above.

DESCRIPTION OF THE EMBODIMENTS

Examples

Example 1: Synthesis of a Polybenzoxazine Monomer from Furfurylaminomethylphenol and Terephthalaldehyde and Subsequent Crosslinking Furfurylamine is reacted with salicylaldehyde in stoichiometric proportions in methanol at reflux for 2 h to form the corresponding imine. The imine is reduced to the amine with 1 equivalent of NaBH$_4$ added at 0° C. in a solution of the imine in MeOH, followed by heating at reflux for 2 h. The furfurylaminomethylphenol thus synthesized is dissolved in toluene with 0.5 equivalents of terephthalaldehyde and refluxed in a Dean-Stark apparatus to remove water generated during the condensation reaction. The reaction is stopped when the conversion of aldehydes has reached its maximum, monitored by proton NMR. After evaporation of the solvent under reduced pressure, the isolated bisbenzoxazine is an off-white solid. The product was characterized by NMR and infrared spectroscopy and the structure was confirmed.

[Chem. 10]

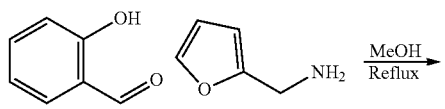

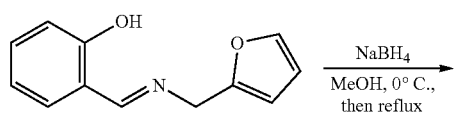

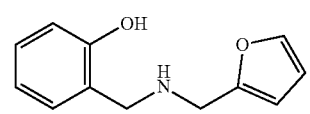

[Chem. 11]

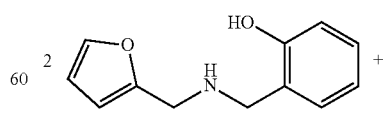

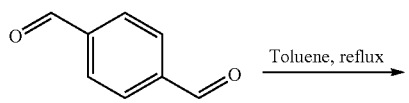

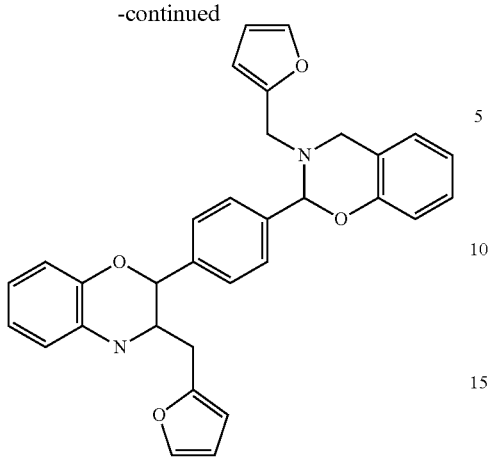
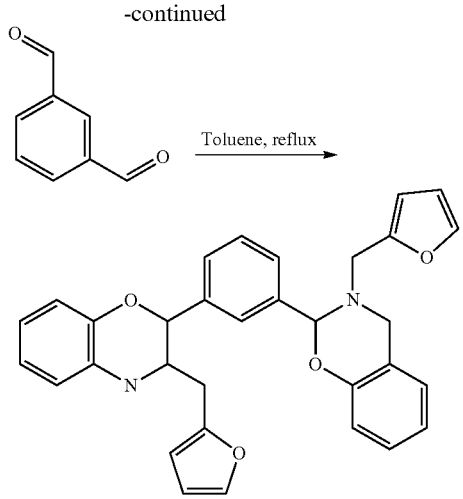

Figure 1:
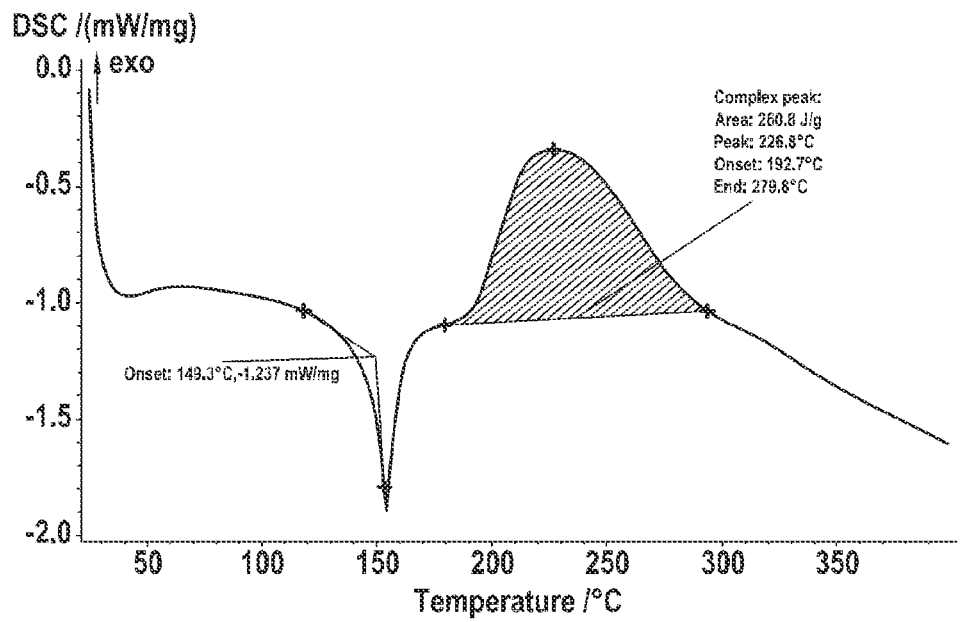
FIG. 1 is a DSC thermogram of an example of a polybenzoxazine monomer of formula C obtained by carrying out the invention.

Thermal characterization by differential scanning calorimetry (DSC) revealed a melting temperature of 150° C. as well as an exothermic reaction between 190° C. and 280° C., representing 261 J/g of enthalpy compared with the reference, with a ramp of 20° C./min in high-pressure sealed steel crucibles. The resulting DSC thermogram is provided in FIG. 1.

Figure 2:
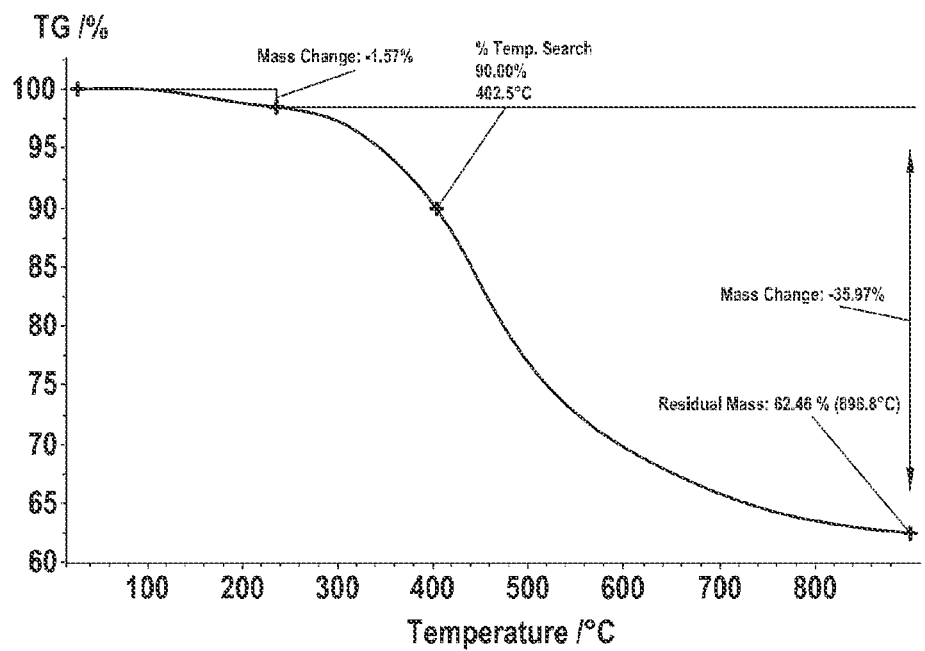
FIG. 2 is a result of thermogravimetric analysis (TGA) of a crosslinked product obtained by crosslinking this polybenzoxazine monomer.

A bisbenzoxazine sample was crosslinked at 180° C. for 4 hours and showed no residual signal in DSC. Thermogravimetric analysis showed a coke content of 62% under nitrogen atmosphere, after 1 h at 900° C. as well as a degradation temperature of 10% of the total mass of 403° C. (heating ramp: 5° C./min). The thermogravimetric analysis graph obtained is provided in FIG. 2. The crosslinked product obtained was insoluble in dichloromethane (the insolubility rate after 24 h at room temperature in dichloromethane, followed by drying under vacuum at 60° C. for 24 h was measured to be 100±0.1%).

Example 2 Synthesis of a Polybenzoxazine Monomer from Furfurylaminomethylphenol and Isophthalaldehyde and Subsequent Crosslinking Furfurylamine is reacted with salicylaldehyde in stoichiometric proportions in methanol at reflux for 2 h to form the corresponding imine. The imine is reduced to the amine with 1 equivalent of NaBH$_4$ added at 0° C. in a solution of the imine in MeOH, followed by heating at reflux for 2 h. The furfurylaminomethylphenol thus synthesized is dissolved in toluene with 0.5 equivalents of isophthalaldehyde and then refluxed in a Dean-Stark apparatus to remove the water generated during the condensation reaction. The reaction is stopped when the conversion of aldehydes has reached its maximum, monitored by proton NMR. After evaporation of the solvent under reduced pressure, the isolated bisbenzoxazine is an off-white solid. The product was characterized by NMR and the structure was confirmed.

[Chem. 12]

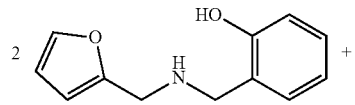

Figure 3:
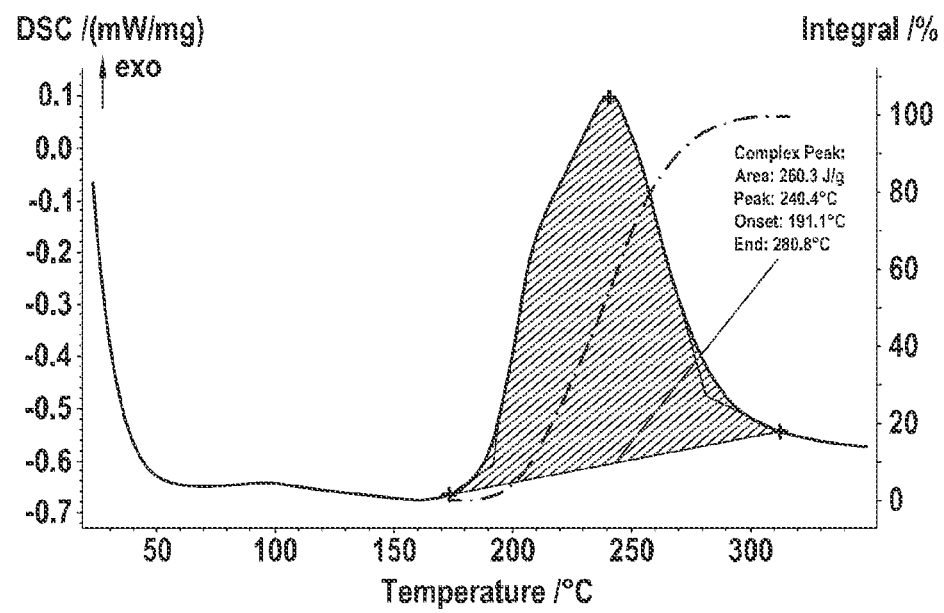
FIG. 3 is a DSC thermogram of an example of a polybenzoxazine monomer of formula C obtained by carrying out the invention.

Thermal characterization by differential scanning calorimetry (DSC) revealed an exothermic reaction between 190° C. and 280° C., representing 260 J/g enthalpy compared with the reference, with a ramp of 10° C./min in high-pressure sealed steel crucibles. The resulting DSC thermogram is provided in FIG. 3.

Figure 4:
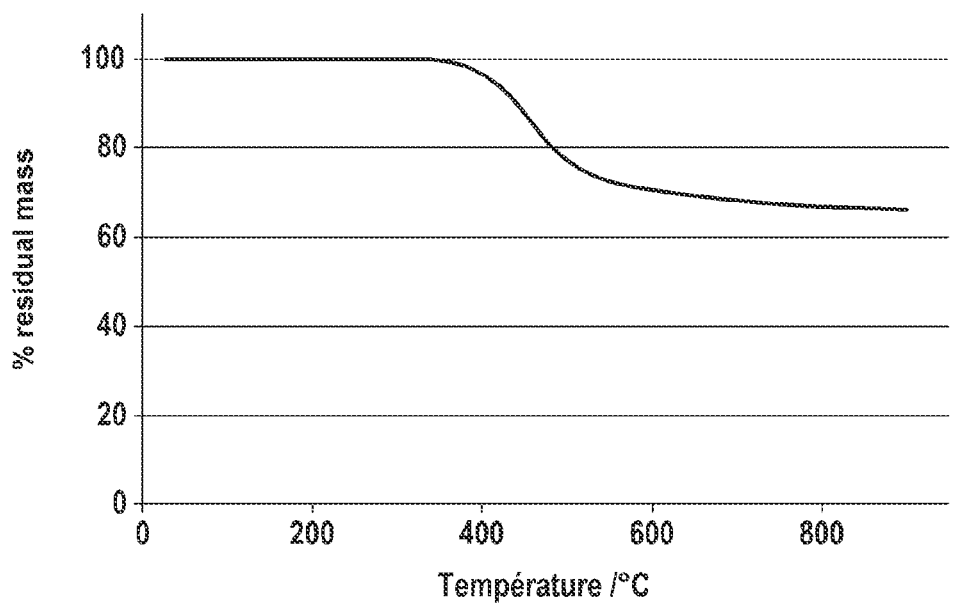
FIG. 4 is a thermogravimetric analysis result of a crosslinked product obtained by crosslinking this polybenzoxazine monomer.

A bisbenzoxazine sample was crosslinked at 200° C. for 10 hours and showed no residual signal in DSC. Thermogravimetric analysis showed a coke content of 66% under nitrogen atmosphere, after 1 h at 900° C. as well as a degradation temperature of 10% of the total mass of 403° C. (heating ramp: 5° C./min). The thermogravimetric analysis graph obtained is provided in FIG. 4.

Example 3: Synthesis of a Polybenzoxazine Monomer from Benzylaminomethylphenol and Terephthalaldehyde and Subsequent Crosslinking Benzylamine is reacted with salicylaldehyde in stoichiometric proportions in methanol at reflux for 2 h to form the corresponding imine. The imine is reduced to the amine with 1 equivalent of NaBH$_4$ added at 0° C. in a solution of the imine in MeOH, followed by heating at reflux for 2 h. The benzylaminomethylphenol thus synthesized is dissolved in toluene with 0.5 equivalents of terephthalaldehyde and then refluxed in a Dean-Stark apparatus to remove the water generated during the condensation reaction. The reaction is stopped when the conversion of aldehydes has reached its maximum, monitored by proton NMR. After evaporation of the solvent under reduced pressure, the isolated bisbenzoxazine is a colorless solid. The product was characterized by NMR and the structure was confirmed.

[Chem. 13]

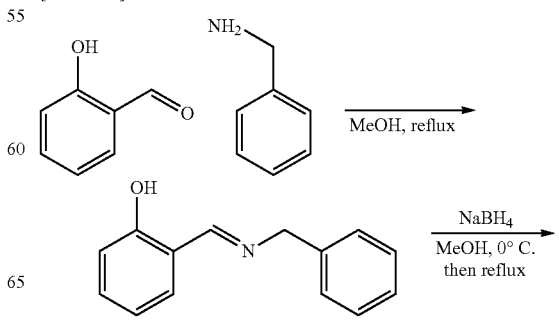

-continued

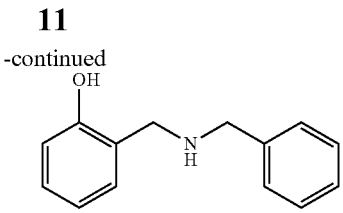

[Chem. 14]

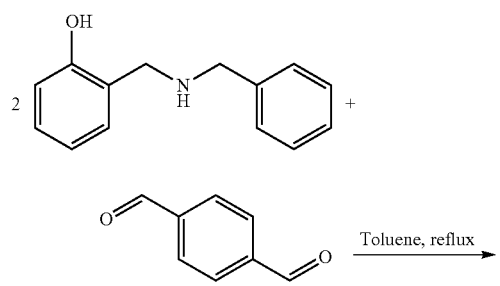

Toluene, reflux

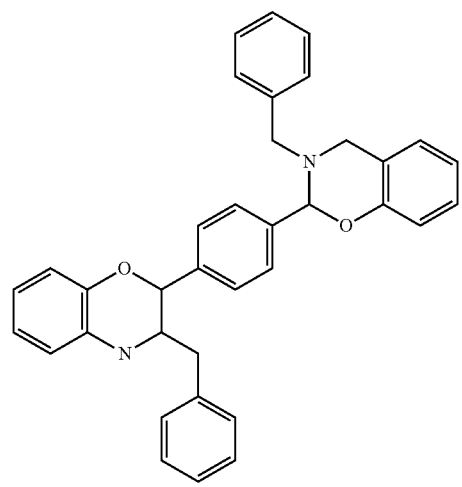

Figure 5:
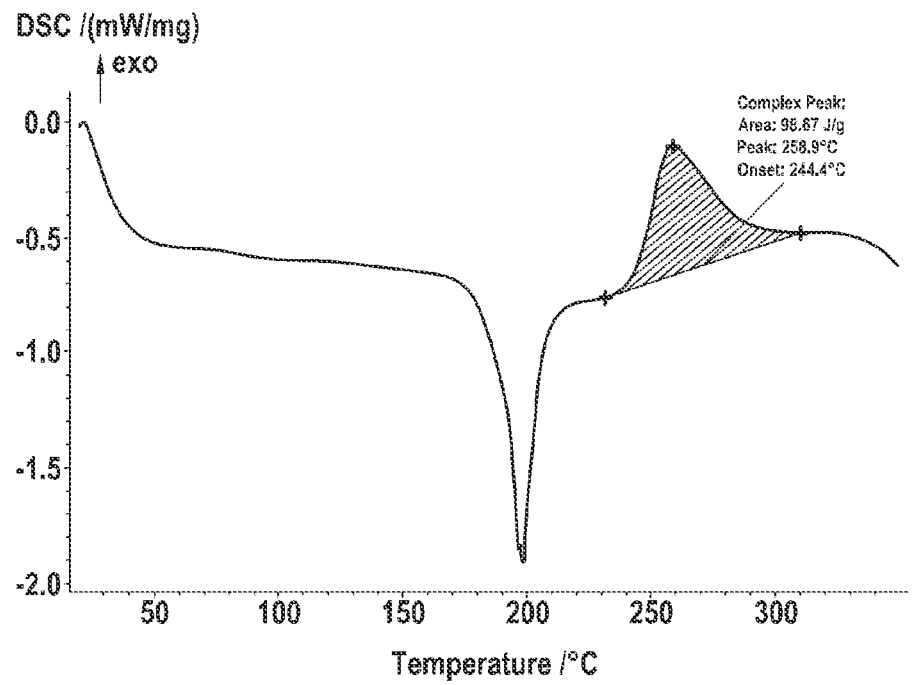
FIG. 5 is a DSC thermogram of an example of a polybenzoxazine monomer of formula C obtained by carrying out the invention.

Thermal characterization by differential scanning calorimetry (DSC) revealed an exothermic reaction between 240° C. and 310° C., representing 99 J/g enthalpy compared with the reference, with a ramp of 10° C./min in high-pressure sealed steel crucibles. The resulting DSC thermogram is provided in FIG. 5.

Figure 6:
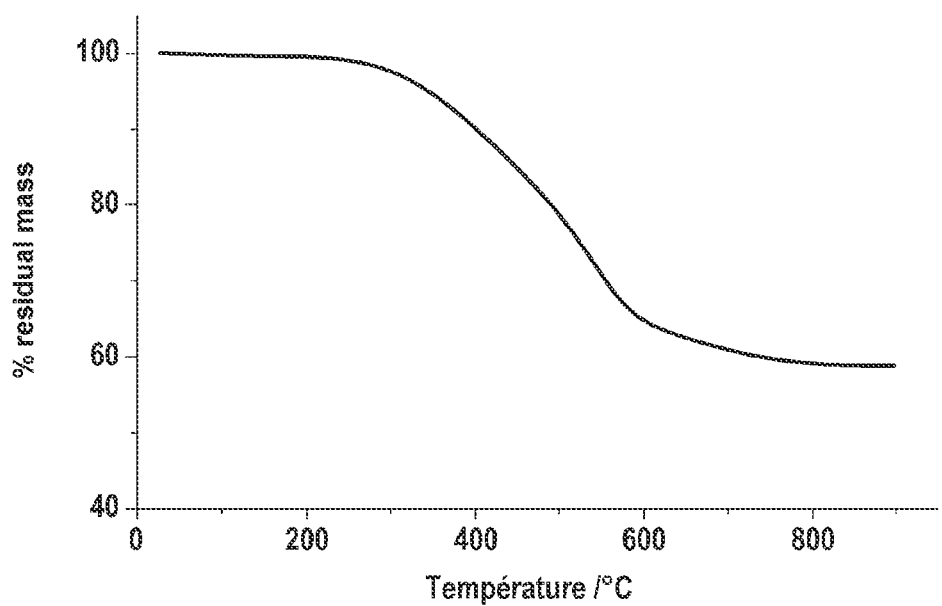
FIG. 6 is a themiogravimetric analysis result of a crosslinked product obtained by crosslinking this polybenzoxazine monomer.

A bisbenzoxazine sample was crosslinked at 200° C. for 7 hours and showed no residual signal in DSC. Thermogravimetric analysis showed a coke content of 59% under nitrogen atmosphere, as well as a degradation temperature of 10% of the total mass of 401° C. (heating ramp: 10° C./min). The thermogravimetric analysis graph obtained is provided in FIG. 6.

Example 4; Study of a Mixture of a Polybenzoxazine Monomer with an Additional Monobenzoxazine Monomer An additional monobenzoxazine monomer was synthesized following a similar procedure as in Example 1 from benzaldehyde and furfuryl aminomethylphenol with 1:1 ratios between these two constituents. The melting temperature of the additional monobenzoxazine monomer is 52° C. The chemical structure of the additional monobenzoxazine monomer obtained is provided below.

[Chem. 15]

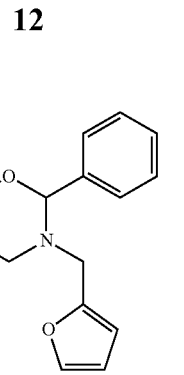

Mixtures of the polybenzoxazine monomer of Example 1 and the additional monobenzoxazine monomer were then prepared. It was found that the viscosity of the resulting mixtures was significantly lower than that of a medium consisting of the polybenzoxazine monomer alone. The monobenzoxazine/polybenzoxazine mass ratios of the prepared mixtures were 25/75, 50/50 and 65/35.

These mixtures of these two benzoxazines were crosslinked at 200° C. for 4 h, resulting in a fully crosslinked material, insoluble in dichloromethane (the rate of insolubility after 24 h at room temperature in dichloromethane, followed by drying under vacuum at 60° C. for 24 h was measured to be 100±0.1%)

The results obtained after thermogravimetric analysis for these crosslinked mixtures are provided in Table 1 below.

TABLE 1

| Mono/poly ratio | Coke content at 900° C. | $T_d$ 10% | Rate of insolubility |
|---|---|---|---|
| 0/100 | 62% | 403° C. | >99.9% ± 0.1% |
| 25/75 | 61% | 392° C. | >99.9% ± 0.1% |
| 50/50 | 58% | 381° C. | >99.9% ± 0.1% |
| 65/35 | 56% | 375° C. | >99.9% ± 0.1% |

Themiogravimetric analysis of the monobenzoxazine/polybenzoxazine mixtures produced showed only a small decrease in coke content compared with the use of polybenzoxazine alone. The degradation temperature of 10% of the total mass ($T_d$10%) was also not significantly affected. These measurements were conducted with a ramp of 10° C./min to 900° C., with a 1 h isotherm at 900° C., under nitrogen atmosphere.

The additional monobenzoxazine monomer synthesized has the advantage of exhibiting a liquid character when heated to moderate temperature. Its addition thus facilitates the obtaining of a liquid phase compared with the use of the polybenzoxazine monomer alone, without significantly affecting the thermal stability and charring properties.

Example 5: Study of a Mixture of a Polybenzoxazine Monomer Synthesized from a Polyaldehyde with an Additional Polybenzoxazine Monomer Synthesized from a Polyamine An additional polybenzoxazine monomer was synthesized from a polyamine in the following manner.

Meta-xylylenediamine is reacted with salicylaldehyde in stoichiometric proportions in methanol at reflux for 2 h to form the corresponding imine. The imine is reduced to the amine with 2 equivalents of NaBH$_4$ added at 0° C. in a solution of the imine in ethanol, heating is then carried out at reflux for 2 hours. The meta-xylylene-aminomethylphenol thus synthesized is dissolved in toluene with 2 equivalents of benzaldehyde and then refluxed in a Dean-Stark apparatus to remove the water generated during condensation. After evaporation of the solvent under reduced pressure, the product obtained is a viscous liquid with an orange color when hot, and a pale yellow solid at room temperature. The product was characterized by NMR and the structure was confirmed,

[Chem. 16]

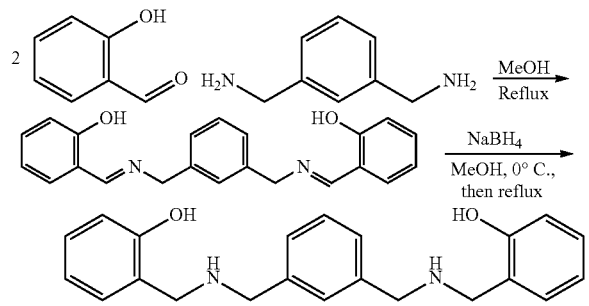

[Chem. 17]

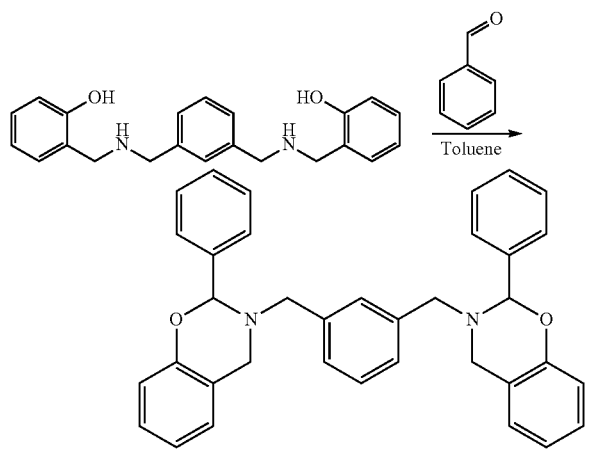

Figure 7:
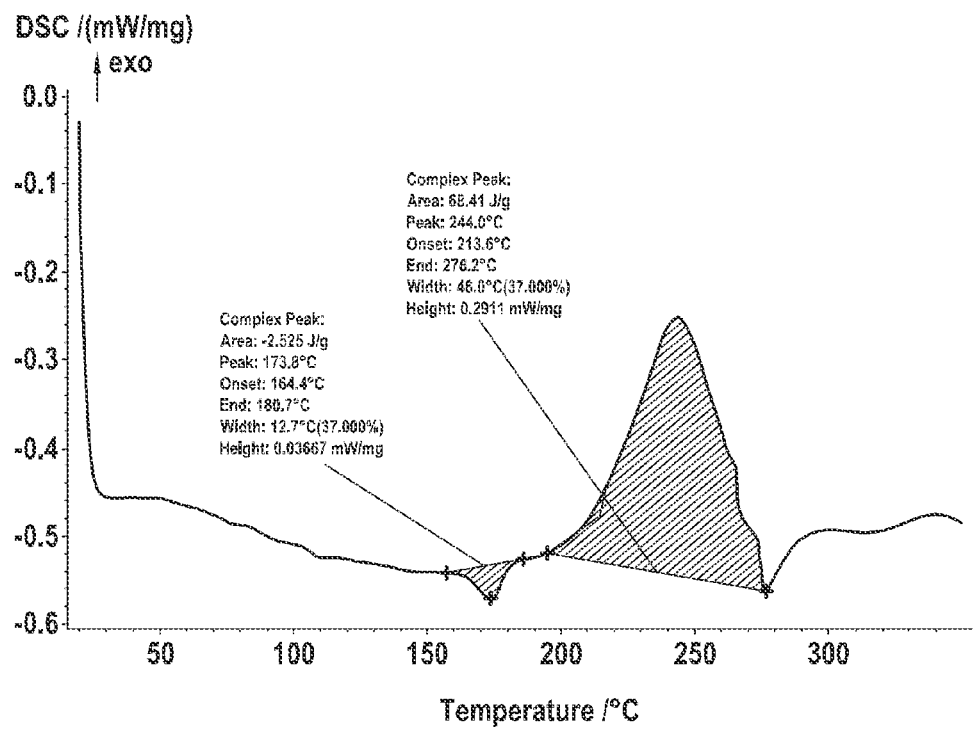
FIG. 7 is a DSC thermogram of an example of an additional polybenzoxazine monomer of formula E suitable for use in the context of the process in accordance with the invention.
Figure 8:
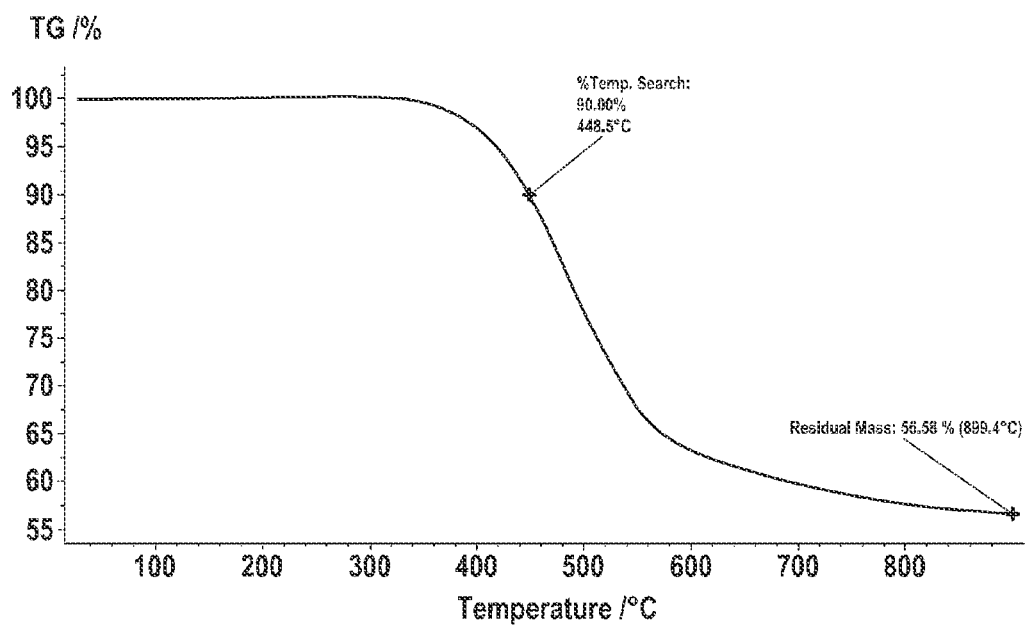
FIG. 8 is a thermogravimetric analysis result of a crosslinked product obtained by crosslinking this polybenzoxazine monomer.

Thermal characterization by DSC revealed an enthalpy of polymerization of 68 Ng. The DSC thermogram obtained is provided in FIG. 7. Thermogravimetric analysis of a crosslinked sample showed a coke content of 57% under nitrogen atmosphere at 900° C. as well as a degradation temperature of 10% of the total mass of 448° C., The thermogravimetric analysis graph obtained is provided in FIG. 8.

The additional polybenzoxazine monomer synthesized from the polyamine was mixed with the polybenzoxazine monomer obtained in Example 1. The additional polybenzoxazine monomer synthesized from the polyamine advantageously exhibits a liquid character when heated to moderate temperature. Its addition thus facilitates the obtaining of a liquid phase compared with the use of the polybenzoxazine monomer of Example 1 alone.

A mixture was made comprising the polybenzoxazine monomer obtained from polyaldehyde in an amount of 25% by mass and the additional polybenzoxazine monomer synthesized from polyamine in an amount of 75% by mass. The mixture was heated to 80° C. using a water bath, then the mixture was homogenized with a spatula and then crosslinked by heat treatment at 200° C.

Thermogravimetric analysis of this crosslinked mixture was performed under nitrogen up to 900° C. The results are provided in Table 2 below. It can be noted that the tested polybenzoxazine mixture has an intermediate coke content between the products crosslinked from pure polybenzoxazines. Adding the additional polybenzoxazine monomer synthesized from the polyamine significantly decreases the viscosity, which facilitates the use of certain types of techniques such as resin transfer molding. In Table 2 below, the additional polybenzoxazine monomer synthesized from the polyamine is denoted "bzx MXDA" and the polybenzoxazine monomer synthesized from the polyaldehyde is denoted "bzx TPA", It is found that the thermal and charring properties of the mixture remain compatible with the application as an ablative resin for thruster nozzles.

TABLE 2

| bzx MXDA/bzx TPA ratio | Coke content at 900° C. | $T_d$ 10% |
|---|---|---|
| 100/0 | 57% | 448° C. |
| 75/25 | 59% | 411° C. |
| 0/100 | 62% | 405° C. |

The expression "comprised between . . . and . . . " should be understood as including the bounds.

The invention claimed is:

1. A process for manufacturing a polybenzoxazine monomer comprising condensing an amine of formula A with a polyaldehyde of formula B in order to obtain the polybenzoxazine monomer of formula C, formulas A, B and C being provided below:

[Chem. 18]

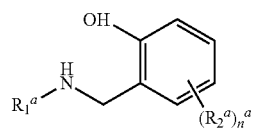

A

[Chem. 19]

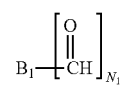

B

[Chem. 20]

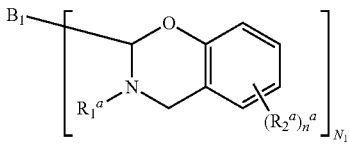

C in these formulas:

$R_1^a$ is a substituted or unsubstituted furfuryl group or a substituted or unsubstituted benzyl group, $R_2^a$ is selected from: electron-withdrawing groups; saturated or unsaturated, substituted or unsubstituted, linear or branched hydrocarbon chains comprising between 1 and 6 carbon atoms, interrupted or not interrupted by one or more heteroatoms; saturated, unsaturated or aromatic, substituted or unsubstituted carbocyclic or heterocyclic groups;

$n^a$ is an integer comprised between 0 and 2;

$B_1$ is selected from: monocyclic or polycyclic, substituted or unsubstituted aromatic carbocyclic or aromatic heterocyclic groups; and $N_1$ is an integer greater than or equal to 2.

2. The process as claimed in claim 1, wherein $n^a$ is equal to 0.

3. The process as claimed in claim 1, wherein $B_1$ is a substituted or unsubstituted benzene ring and, in this case, $N_1=2$ or 3.

4. The process as claimed in claim 1, wherein $N_1$ is an integer equal to 2.

5. A process for manufacturing a crosslinked product comprising:
   manufacturing a polybenzoxazine monomer of formula C by carrying out the process as claimed in claim 1, and crosslinking the polybenzoxazine monomer of formula C.

6. The process as claimed in claim 5, comprising crosslinking of a mixture comprising the polybenzoxazine monomer of formula C and an additional monobenzoxazine monomer of formula D, formula D being provided below:

[Chem. 21]

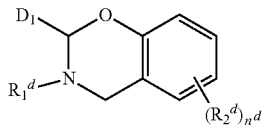

formula in which:
$R_1^d$ is selected from: substituted or unsubstituted furfuryl groups; saturated, unsaturated or aromatic, monocyclic or polycyclic, substituted or unsubstituted carbocyclic or heterocyclic groups; substituted or unsubstituted aralkyl groups; saturated or unsaturated, substituted or unsubstituted, linear or branched hydrocarbon chains, interrupted or not interrupted by one or more heteroatoms or by one or more saturated, unsaturated or aromatic, monocyclic or polycyclic, substituted or unsubstituted carbocyclic or heterocyclic groups;

$R_2^d$ is selected from: electron-withdrawing groups; saturated or unsaturated, substituted or unsubstituted, linear or branched hydrocarbon chains comprising between 1 and 6 carbon atoms, interrupted or not interrupted by one or more heteroatoms; saturated, unsaturated or aromatic, substituted or unsubstituted carbocyclic or heterocyclic groups;

$n^d$ is an integer comprised between 0 and 2;

$D_1$ is selected from: saturated, unsaturated or aromatic, monocyclic or polycyclic, substituted or unsubstituted carbocyclic or heterocyclic groups; linear or branched, saturated or unsaturated, substituted or unsubstituted hydrocarbon chains, interrupted or not interrupted by one or more heteroatoms.

7. The process as claimed in claim 5, wherein there is crosslinking of a mixture comprising the polybenzoxazine monomer of formula C and an additional polybenzoxazine monomer of formula E, formula E being provided below:

[Chem. 22]

in this formula E:
$N_2$ is an integer greater than or equal to 2;
$E_2$ is selected from saturated or unsaturated, substituted or unsubstituted, linear or branched hydrocarbon chains interrupted by one or more heteroatoms or by one or more saturated, unsaturated or aromatic, monocyclic or polycyclic, substituted or unsubstituted, carbocyclic or heterocyclic groups, or uninterrupted;

the groups of formula $E_1$ are identical or different and each has the formula below:

[Chem. 23]

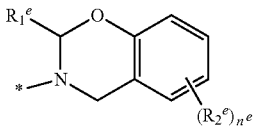

in this formula $E_1$:
$R_1^e$ is selected from: saturated, unsaturated or aromatic, monocyclic or polycyclic, substituted or unsubstituted carbocyclic or heterocyclic groups; linear or branched, saturated or unsaturated, substituted or unsubstituted hydrocarbon chains, interrupted or not interrupted by one or more heteroatoms; and $R_2^e$ is selected from: electron-withdrawing groups; saturated or unsaturated, substituted or unsubstituted, linear or branched hydrocarbon chains comprising between 1 and 6 carbon atoms, interrupted or not interrupted by one or more heteroatoms; saturated, unsaturated or aromatic, substituted or unsubstituted carbocyclic or heterocyclic groups;

$n^e$ is an integer comprised between 0 and 2;

*—denotes the bond to $E_2$.

8. A process for manufacturing a thruster nozzle comprising manufacturing the crosslinked product by carrying out the process as claimed in claim 5 and manufacturing the nozzle with said crosslinked product.

9. A process for manufacturing an atmospheric reentry body comprising manufacturing the crosslinked product by carrying out the process as claimed in claim 5 and manufacturing the atmospheric reentry body with said crosslinked product.

* * * * *